United States Patent [19]
Gousset et al.

[11] Patent Number: 5,840,333
[45] Date of Patent: Nov. 24, 1998

[54] PROCESS FOR THE PREPARATION OF ORAL COMPOSITIONS CONTAINING QUINOLONES

[75] Inventors: Gabriel Gousset, Les Plessis Robinson; Philippe Riviere, Chatenay-Malabry, both of France

[73] Assignee: Rhone-Poulenc Rorer S.A., Antony, France

[21] Appl. No.: 632,394

[22] PCT Filed: Oct. 19, 1994

[86] PCT No.: PCT/FR94/01211

§ 371 Date: Apr. 19, 1996

§ 102(e) Date: Apr. 19, 1996

[87] PCT Pub. No.: WO95/11022

PCT Pub. Date: Apr. 27, 1995

[30] Foreign Application Priority Data

Oct. 21, 1993 [FR] France .................................. 93 12550

[51] Int. Cl.⁶ .......................... A61K 31/44; A61K 31/47; A61K 31/495; A61K 9/20

[52] U.S. Cl. .......................... 424/464; 424/470; 424/474; 264/115; 264/117; 264/118; 264/122; 514/311; 514/781; 514/960

[58] Field of Search ..................................... 264/115, 117, 264/118, 122; 424/470, 474, 464; 514/311, 781, 960

[56] References Cited

U.S. PATENT DOCUMENTS

| | | | |
|---|---|---|---|
| 4,639,458 | 1/1987 | Katdare | 514/311 |
| 4,973,470 | 11/1990 | Mills et al. | 424/467 |

OTHER PUBLICATIONS

English language Derwent Abstract of JP 1175936.

*Primary Examiner*—Frederick Krass
*Attorney, Agent, or Firm*—Finnegan, Henderson, Farabow, Garrett & Dunner, L.L.P.

[57] ABSTRACT

Method for the preparation of an improved oral formulation of active ingredients belonging to the class of quinolones. The method is characterized by an intermediate compacting and grinding stage, before compression of the mixture of the active ingredient and excipients.

5 Claims, 2 Drawing Sheets

PROCESS FOR THE PREPARATION OF ORAL COMPOSITIONS CONTAINING QUINOLONES

The present invention relates to a process for the preparation of an oral formulation of products belonging to the quinolone family.

The products of the quinolone family are widely known antibacterial agents, which have been described in particular in the following references: BE 870 576; U.S. Pat. No. 4,448,962; DE 3 142 854; EP 047 005; EP 206 283; BE 887 574; EP 221 463; EP 140 116; EP 131 839; EP 154 780; EP 078 362; EP 310 849; EP 520 240; U.S. Pat. No. 4,499,091; U.S. Pat. No. 4,704,459; U.S. Pat. No. 4,795,751; U.S. Pat. No. 4,668,784.

The preparation of fine granules by a wet granulation process has been described in the publication by Y. Shirai et al., Biol. Pharm. Bull. 16(2), 172 (1993).

A process for the direct compression of the mixture of a quinolone with excipients, without the prior addition of mixing water, has been described in Patent EP 189,114.

However, the previously known processes have drawbacks which lead, most often, to an imperfect result. Indeed, the processes which make use of wet granulation have a tendency to slow down the dissolution and to promote the formation of hydrates, which are less soluble or more difficult to disperse when compared with the corresponding anhydrous form. This results in a delay in the dissolution and the release of the active principle, which may be a nuisance in the use of antimicrobial medicinal products. Moreover, methods for the direct compression of a mixture of the excipients in powder form has the advantage of avoiding the formation of hydrates, but the quality of the tablets obtained is not always consistent and satisfactory insofar as cleavage problems arise, thus rendering some batches of tablets unsuitable for marketing. Industrial losses, which may prove to be considerable, are thereby incurred.

It has now been found that oral formulations of active principles belonging to the quinolone family, having no problems of overly slow solubilization or any cleavage problems, could be prepared by incorporating an intermediate step of compacting and then of grinding. Namely, by dry-mixing the said active principle with the suitable excipients for an oral formulation, followed by a compacting, a grinding and then compression of the granules thus obtained. The new step of compacting and grinding makes it possible to carry out the direct compression of a powder of much coarser particle size and leads to tablets having no cleavage problems. The industrial risks due to batch-to-batch variations were thus able to be reduced, or even eliminated.

According to the invention, the products of quinolone family may be chosen from the products of general formula:

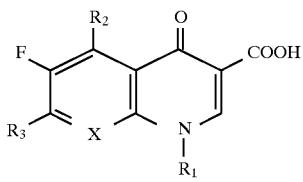

in which
$R_1$ is an alkyl radical containing 1 to 4 carbon atoms or a fluoroethyl, cyclopropyl, methylamino or difluorophenyl radical, X represents a nitrogen atom or a group $=CR_7-$ in which $R_7$ is a hydrogen, chlorine or fluorine atom or alternatively $R_7$ forms, with the radical $R_1$ and the atoms to which they are attached, a 6-membered heterocycle which is substituted with a methyl radical and which optionally contains an oxygen or sulphur atom, $R_2$ is a hydrogen atom or may represent an amino radical if $R_7$ is a fluorine atom, and $R_3$ is a hydrogen atom, a 2,8-diazabicyclo[4.3.0]non-8-yl radical or a radical of structure:

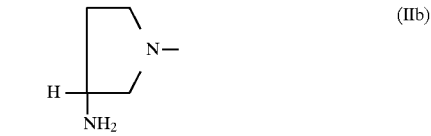

in which $R_4$, $R_5$ and $R_6$ are identical or different and represent hydrogen atoms or methyl radicals, or the pharmaceutically acceptable salts thereof.

More especially advantageous among the quinolones mentioned above are pefloxacin, sparfloxacin, ciprofloxacin, ofloxacin, levofloxacin, enoxacin, norfloxacin, fleroxacin, lomefloxacin, temafloxacin, amifloxacin, tosufloxacin, flumequine, rufloxacin, clinafloxacin, Bay-y-3118 and PD 131 628.

According to the process of the invention, the compacting is carried out by subjecting the product to a mechanical densification at a rather low force, followed by grinding the agglomerates thus obtained on a grid, in order to obtain a mixture having a particle size of 50 μm to 1 mm and preferably greater than 100 μm, thus allowing a good flow and good uniformity in the doses.

The mechanical densification may be carried out at a force ranging from 1 to 12 kg N/cm. Preferably at a force of 1 to 5 kg N/cm. The grid on which the grinding is carried out is such that it is possible to ensure that the abovementioned particle size is obtained.

The excipients used are generally those which are usually recommended for the direct compression of a mixture of powders. By way of example, the excipients are chosen in particular from cohesion agents, cleaving agents, flow agents and lubricants.

More precisely, and without any limitation being implied, the cohesion agents may be microcrystalline cellulose, lactose, calcium hydrogen phosphate or mixtures of these excipients; the cleaving agents may be corn starch, wheat starch, L-hydroxypropyl cellulose, sodium carboxymethyl starch, crosslinked sodium carboxymethyl cellulose or mixtures of these excipients; the flow agents may be colloidal silica, talc or mixtures of these excipients; the lubricants may be magnesium stearate, stearic acid, glycerol tribehenate or mixtures of these excipients.

According to the invention, the compression operation which follows the compacting and the grinding is carried out at a force which may range from 6 to 10 kN (measured at the compression roller) and preferably of the order of 8 to 9 kN. This compression operation is preferably preceded by a precompression at a force which may range from 0.5 to 2.5 kN.

High compression rates may be achieved by virtue of the process according to the invention, without, however, detrimentally affecting the quality of the tablets. It is in particular possible to reach rates higher than 150,000 tablets/hour, without causing any cleavage.

The tablets thus obtained have a disintegration time of less than 1 minute and generally of the order of 30 seconds. Their residual moisture content is generally in the region of 2.4% and may vary from 2.1 to 3%.

It is understood that the tablets obtained on conclusion of the process according to the invention may optionally be film-coated according to the usual methods. The film-coating operation is facilitated by the fact that no cleavage occurs during the operation.

The process according to the invention makes it thus possible to gain access to an oral form in which cleavage is suppressed, in which the tablets show increased homogeneity of hardness and in which the mixture used in the final compression, after the compacting and the grinding, shows increased cohesion.

The absence of cleavage zones was demonstrated in particular in the following test: An interchangeable ground drill bit, rotating at a steady speed set at 500 revolutions per minute, penetrates vertically into the tablet which is mounted on a holder which rises steadily and continuously (1 mm/minute). Simultaneously, a detector connected to a strain gauge placed under the tablet holder records the forces which oppose the advancement of the bit into the tablet. The sudden variations in the forces recorded indicate the presence of a cleavage zone. In the tests carried out on the tablets of Examples 1 to 3, no cleavage was observed.

The examples which follow, given without any limitation being implied, illustrate the present invention.

EXAMPLE 1

1) The constituents intended for the initial mixture, comprising:

| | |
|---|---|
| sparfloxacin | 6,666.67 g |
| microcrystalline cellulose | 1,566.67 g |
| corn starch | 1,000.00 g |
| L-hydroxypropyl cellulose | 333.33 g |
| colloidal silica | 100.00 g | are screened through a 1 mm grid and then mixed in a 30-liter tank for 15 minutes at a speed of 12 rotations per minute (rpm).

After screening through a 0.5 mm grid, 133.33 g of magnesium stearate are added, following by mixing for a further 5 minutes at a speed of 12 rotations per minute.

2) The powder mixture is compacted and then ground on a Gerteis® compacter (3W Polygran type) set to the following parameters:
   a) compacting:
      pressure on the rollers: 2.4 kN/cm
      thickness of the compact: 3.0 mm
      roller speed: 12 rpm
      % of briquette: 90%
   b) grinding:
      compactor equalizing grid: 1.00 mm
      speed of the equalizing rotor: 40 rpm
      amplitude of the equalizing rotor: 60°.

The yield of the operation is approximately 80 kg/hour.

After mixing the ground material for 10 minutes, 100 g of L-hydroxypropyl cellulose, screened beforehand through a 0.5 mm grid, are added. Mixing is continued for 10 minutes at the speed of 12 rpm, and 100 g of magnesium stearate, screened beforehand through a 0.5 mm grid, are then added. Mixing is continued for a further 5 minutes at the speed of 12 rpm.

3) The compression is carried out on a Courtoy® R190 rotary machine equipped with 24 punches of 8 mm diameter and of a 10 mm radius of curvature. The precompression is carried out at a force of 250 kg and the compression is carried out at a force of 780 kg. The production rate is 1000 tablets of unit mass: 150 mg per minute.

Good flow of the powder, good weight behaviour and a correct hardness of the tablets are observed. There is no presence of cleavage zones.

Figure 1:
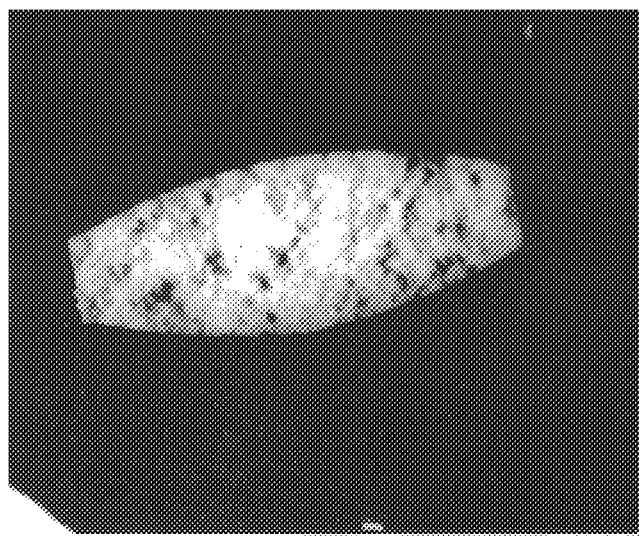
FIGS. 1, 2 and 3 are photographs of compressed granules prepared by the method of the invention and show a lack of cleavage zones.

FIG. 1 shows the absence of cleavage zones (magnification: 7.5).

EXAMPLE 2

1) The constituents intended for the initial mixture, comprising:

| | |
|---|---|
| sparfloxacin | 40,000 g |
| microcrystalline cellulose | 9,400 g |
| corn starch | 6,000 g |
| L-hydroxypropyl cellulose | 2,000 g |
| colloidal silica | 600 g | are screened through a 1 mm grid and then mixed in a 30-liter tank for 15 minutes at the speed of 12 rotations per minute (rpm).

After screening through a 0.5 mm grid, 800 g of magnesium stearate are added, followed by mixing for a further 5 minutes at the speed of 12 rotations per minute.

2) The mixture of powders is compacted and then ground on a Gerteis® compacter (3W Polygran type) set to the following parameters:
   a) compacting:
      pressure on the rollers: 2.4 kN/cm
      thickness of the compact: 3.0 mm
      roller speed: 12 rpm
      % of briquette: 90%
   b) grinding:
      compactor equalizing grid: 1.00 mm
      speed of the equalizing rotor: 40 rpm
      amplitude of the equalizing rotor: 60°

The yield of the operation is approximately 80 kg/hour.

After mixing the ground material for 10 minutes, 600 g of L-hydroxypropyl cellulose, screened beforehand through a 0.5 mm grid, are added. Mixing is continued for 10 minutes at the speed of 12 rpm, and 600 g of magnesium stearate, screened beforehand through a 0.5 mm grid, are then added. Mixing is continued for a further 5 minutes at the speed of 12 rpm.

3) The compression is carried out on a Courtoy® R190 rotary machine equipped with 24 punches of 8 mm diameter and of a 10 mm radius of curvature. The precompression is carried out at a force of 160 kg and the compression is carried out at a force of 800 kg. The production rate is 1500 tablets of 150 mg per minute.

Good flow of the powder, good weight behaviour and a correct hardness of the tablets are observed. There is no presence of cleavage zones.

Figure 2:
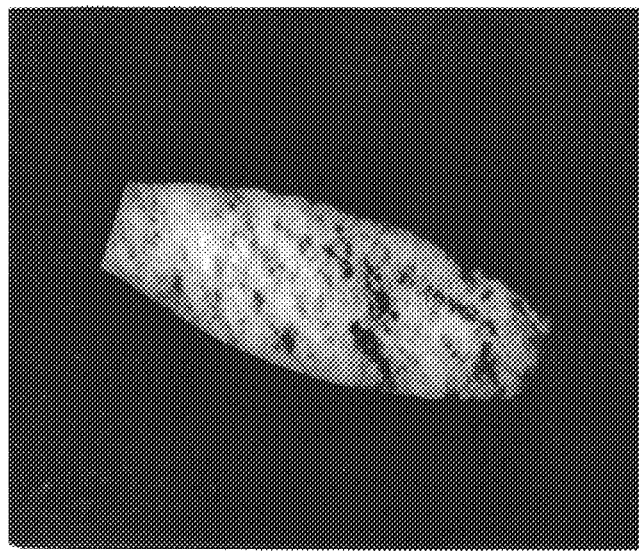

FIG. 2 shows the absence of cleavage zones (magnification: 7.5).

EXAMPLE 3

1) The constituents intended for the initial mixture, comprising:

| | |
|---|---|
| sparfloxacin | 166.667 kg |
| microcrystalline cellulose | 39.167 kg |
| corn starch | 25.000 kg |
| L-hydroxypropyl cellulose | 8.333 kg |
| colloidal silica | 2.500 kg | are placed in a 600-liter tank feeding a screener fitted with a 0.24 cm grid. After screening, the powders are collected in another 600-liter mixer tank. The powders are mixed for 15 minutes at a speed of 8 rotations per minute. After screening through a 0.11 cm grid, 3.333 kg of magnesium stearate are added, followed by continued stirring of the mixture for 5 minutes at the speed of 8 rotations per minute.

2) The mixture of powders is compacted and then ground on a Gerteis® compacter (3W Polygran type) set to the following parameters:
   a) compacting:
      pressure on the rollers: 2.4 kN/cm
      thickness of the compact: 3.0 mm
      roller speed: 12 rpm
      % of briquette: 90%
   b) grinding:
      compactor equalizing grid: 1.00 mm
      speed of the equalizing rotor: 50 rpm
      amplitude of the equalizing rotor: 90°

The yield of the operation is approximately 80 kg/hour.

After mixing the ground material for 2 minutes, 2.500 kg of L-hydroxypropyl cellulose, screened beforehand through a 0.11 cm grid, are added. Mixing is continued for a further 5 minutes at the speed of 8 rpm.

3) The compression is carried out on a Fette PT2080® rotary machine equipped with 43 punches of 10 mm diameter and of a 12 mm radius of curvature. The precompression is carried out at a force of 1.5 kN and the compression is carried out at a force of 8.5 kN. The production rate is 80,000 tablets of 300 mg per hour.

Good flow of the powder, good weight behaviour and a correct hardness of the tablets are observed. There is no presence of cleavage zones.

Figure 3:
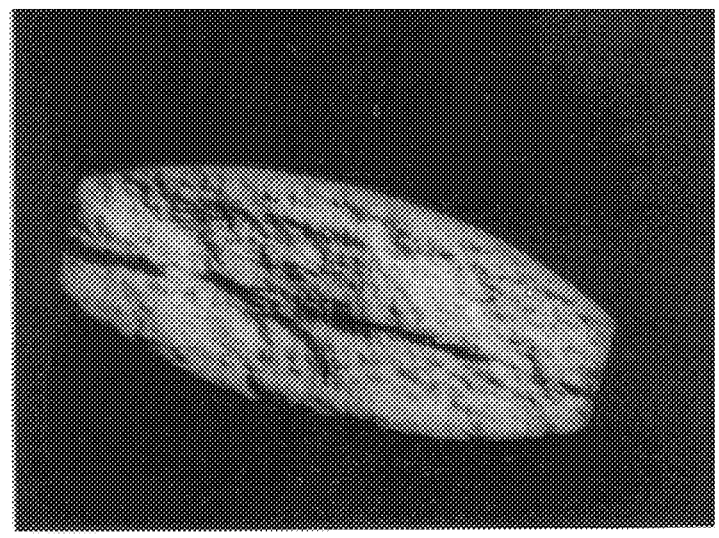
Figure 4:
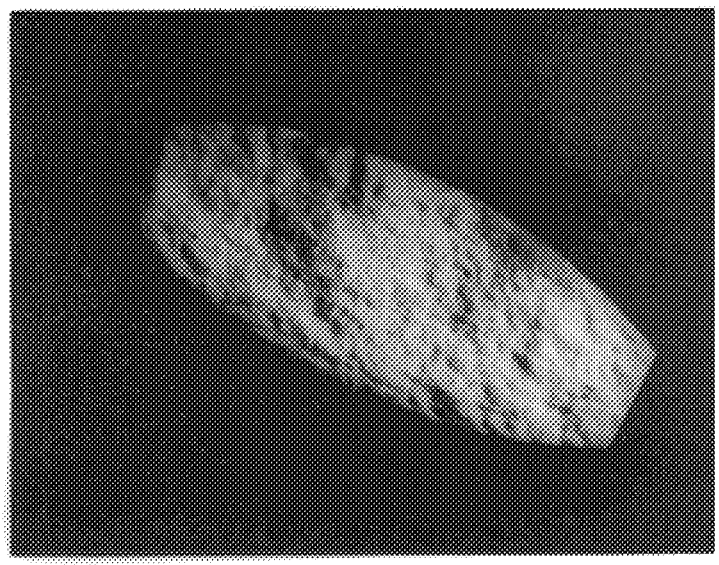
FIG. 4 is comparative and is a photograph of a directly compressed granule and shows a cleavage zone.

FIG. 3 shows the absence of cleavage zones. FIG. 4 shows a cleavage zone on a tablet prepared in identical proportions to those of Example 3, but by direct compression of the powder mixture (magnification: 7.5).

We claim:

1. A process for preparing an oral antibacterial formulation of quinolone active principles, which comprises the steps of:
   compacting at least one quinolone active principle and at least one excipient suitable for oral formulation into a mixture;
   grinding the compacted mixture into granules wherein said granules have a particle size ranging from 50 μm to 1 mm; and
   compressing the granules.

2. A process for preparing an oral antibacterial formulation of quinolone active principles, which comprises the steps of:
   dry-mixing at least one quinolone active principle and at least one excipient suitable for an oral formulation,
   compacting the dry mixture;
   grinding the compacted mixture to form granules wherein said granules have a particle size ranging from 50 μm to 1 mm;
   optionally precompressing the compacted granules; and
   compressing the granules.

3. A process according to claim 1, wherein said compacting step comprises mechanical densification carried out at a force ranging from 1 to 12 kg N/cm, and said grinding step comprises grinding to ensure a particle size of 50 μm to 1 mm.

4. A process according to claim 1, wherein said quinolone active principle is selected from compounds of formula:

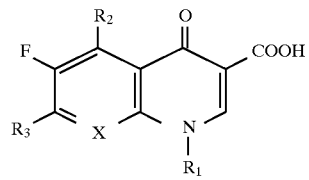

in which $R_1$ represents an alkyl radical containing from 1 to 4 carbon atoms or a fluoroethyl, cyclopropyl, methylamino or difluorophenyl radical;

X represents a nitrogen atom or a $=CR_7-$ group in which $R_7$ represents a hydrogen, chlorine or fluorine atom, or $R_7$ forms, with the radical $R_1$ and the atoms to which they are attached, a 6-membered heterocycle that is substituted with a methyl radical and may contain an oxygen or sulphur atom;

$R_2$ represents a hydrogen atom or represents an amino radical if $R_7$ represents a fluorine atom;

$R_3$ represents a hydrogen atom, a 2,8-diazabicyclo[4.3.0] non-8-yl radical or a radical having the structure:

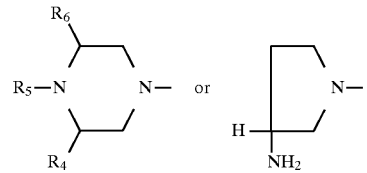

in which $R_4$, $R_5$ and $R_6$ are identical or different and represent hydrogen atoms or methyl radicals, or the pharmaceutically acceptable salts of said compounds.

5. A tablet for oral administration of quinolone active principles, which comprises the oral formulation prepared according to the process of claim 1.

* * * * *